United States Patent
Kanai (10) Patent No.: US 6,807,531 B1
(45) Date of Patent: Oct. 19, 2004

(54) SUPPORT SYSTEM FOR MAKING DECISIONS ON MEDICAL TREATMENT PLANS OR TEST PLANS

(75) Inventor: Kazuyuki Kanai, Kasai (JP)

(73) Assignee: Sysmex Corporation, Kobe (JP)

( * ) Notice: Subject to any disclaimer, the term of this patent is extended or adjusted under 35 U.S.C. 154(b) by 388 days.

(21) Appl. No.: 09/288,504

(22) Filed: Apr. 8, 1999

(30) Foreign Application Priority Data

Apr. 8, 1998 (JP) .......................................... 10-135885

(51) Int. Cl.$^7$ ............................................ G06F 17/60
(52) U.S. Cl. ...................................................... 705/2
(58) Field of Search .................. 705/2, 3; 600/300; 703/11; 706/15

(56) References Cited

U.S. PATENT DOCUMENTS 4,839,822 A * 6/1989 Dormond et al. ........... 364/513
5,005,143 A * 4/1991 Altschuler et al. .......... 364/554

FOREIGN PATENT DOCUMENTS

WO    WO 00/07131 A1 * 10/2000       G06F/19/00

OTHER PUBLICATIONS

Ulvila and Brown, Decision Analysis Comes of Age, Sep./Oct. 1982, Harvard Business Review, pp. 130–139.*
Vincze, Expert Choice, Mar. 1990, Software Review, pp. 10–12.*

Colucciello, Clinical pathways in subacute care settings, Jun. 1997, Nursing Management, vol. 28 No. 6, pp. 52–54.*

Fukui, Tsuguya, Jpn. J. Clin. Pathol. 40, 35–41, 1992 "Medical Decision Sciences in the Context of Clinical Pathology".

* cited by examiner

Primary Examiner—Joseph Thomas
Assistant Examiner—Christopher L. Gilligan
(74) Attorney, Agent, or Firm—Birch, Stewart, Kolasch & Birch, LLP (57) ABSTRACT

A support system for making decisions on medical treatment plans or test plans includes using a decision tree having branches that represent actions to be selected in deciding the medical treatment plans or test plans for a person to be inspected and events that may possibly occur as a result of the selected actions, and calculating expectations of the actions to be selected in accordance with occurrence probabilities with which the respective events occur and utility values which reflect intentions of the person to be inspected on the events. The occurrence probabilities of the branches are renewable in accordance with attribute information of the person to be inspected.

26 Claims, 5 Drawing Sheets

SUPPORT SYSTEM FOR MAKING DECISIONS ON MEDICAL TREATMENT PLANS OR TEST PLANS

CROSS-REFERENCES TO RELATED APPLICATIONS

This application is related to Japanese patent application No. HEI 10-135885 filed on Apr. 8, 1998 whose priority is claimed under 35 USC §119, the disclosure of which is incorporated herein by reference in its entirety.

BACKGROUND OF THE INVENTION

1. Field of the Invention

The present invention relates to a support system for making decisions on medical treatment plans or test plans, and more particularly to a system for providing a support in deciding a medical treatment plan or a test plan for a person to be inspected.

2. Description of the Related Art

In clinical medicine, selection from a variety of treatment plans or test plans must often be made in a short time. However, at present, medical services still depend much on experience and intuition of a clinician. Therefore, even if a standard for making such a selection is given, it is often difficult to find out the basis on which the standard has been made.

Further, the results occurring from a selected treatment plan or the like varies from patient to patient, so that the results of the same treatment may vary from complete cure to failure depending on factors such as complication accompanying the treatment, side effects of pharmaceuticals, unsuccessful surgical operations and the like.

In deciding a treatment plan, the clinician must make a selection based on a more definite logical structure by clearly recognizing the possibility that each treatment may cause undesirable results with a certain probability. In order to solve this problem, EBM (Evidence Based Medicine) is proposed in which a suitable procedure (basically a randomized controlled trial) is taken to obtain results referred to as "evidence" and the decisions on the medical treatment plans or test plans are made based on the evidence.

EBM makes it possible to perform a statistically appropriate treatment based on objective data. Also, EBM is expected to contribute to reduction of medical expenses, such reduction being a worldwide trend in recent years.

At present, as evidence for EBM, there are individually descriptions of papers themselves, documents containing summaries of papers, and documents made into protocols. However, EBM has not reached a level such that the total circumstances are grasped by covering various clinical situations for practical clinical application.

Accordingly, a proposal is made in which complicated clinical situations are shown as a "decision tree" in a comprehensive manner by converting such evidence into protocols. According to this method, a decision tree is prepared to calculate expectations of nodes (branching points) on the decision tree based on occurrence probabilities of branches of the decision tree and utility values of leaves at terminal ends of the decision tree, whereby a node having the largest expectation is selected (See "Medical Decision Sciences in the context of Clinical Pathology", Tsuguya Fukui et al., 1991).

However, even if a lot of evidence is made into protocols, it is difficult to utilize these protocols effectively in clinical medicine due to various factors that fluctuate the evidence. For example, due to the substantial development of treatment methods, inspection methods and the like in recent years, evidence that does not reflect this development may be totally unusable. Also, these treatment methods and test methods may vary depending on the institution in which they are used, so that the evidence may also vary from institution to institution. Moreover, simple statistical data of a total group of patients does not reflect the individual condition of each patient, such as the difference in age and sex, other diseases of the patient, the effects of pharmaceuticals and the like.

Therefore, it is difficult to use the evidence in clinical medicine unless the evidence reflects these factors.

Also, various medical decisions have previously been made using a simple criterion of life or death based on a survival rate. However, in recent years, such decisions must be made in accordance with various subjective senses of value of the patient on the health conditions occurring as a result of a treatment in view of QOL (quality of life).

For example, in a mastectomy for treating breast cancer, the selection of a treatment may vary depending on the sense of value of the patient on the mastectomy. The problem is how such a subjective sense of value of the patient can be incorporated in a process for making decisions such as selection of a medical treatment or test.

Furthermore, there is a trend that the decision power for selecting one of a plurality of treatment methods is transferred to the patient side after allowing the patient to fully understand the advantages and disadvantages of each of the treatment methods. This necessitates an "informed consent".

However, if a decision making support system using, for example, a neuro-network is adopted, there arises a problem that it is almost impossible to explain a decision making process to a patient because the decision making process is made into a black box.

SUMMARY OF THE INVENTION

The present invention has been made in view of these circumstances and the purpose thereof is to provide a system capable of (1) providing renewed evidence by successively introducing the latest data, (2) providing the optimal evidence for each patient, (3) supporting a flexible decision making process that meets the various needs (sense of values) of individual patients as well as providing statistically good medical services, (4) further supporting the "informed consent" and (5) supporting the realization of highly efficient medical services in clinical medicine while allowing the system to be based on EBM and, more generally, a system for supporting human decision-making processes by creating a decision tree having a decision criterion that conforms best to the intended object in various situations.

Accordingly, the present invention provides a support system for making decisions on medical treatment plans or test plans, comprising using a decision tree including branches that represent actions to be selected in deciding the medical treatment plans or test plans for a person to be inspected and events that may possibly occur as a result of the selected actions, and calculating expectations of the actions to be selected in accordance with occurrence probabilities with which the respective events occur and utility values which reflect intentions of the person to be inspected on the events, wherein the occurrence probabilities of the branches are renewable in accordance with attribute information of the person to be inspected.

BRIEF DESCRIPTION OF THE DRAWINGS

The present invention will be better understood from the following detailed description of preferred embodiments of the invention, taken in conjunction with the accompanying drawings, in which.

DETAILED DESCRIPTION OF THE PREFERRED EMBODIMENTS

Judgment information in a support system of the present invention is embodied as a tree structure of a decision tree having a plurality of branches, occurrence probabilities of the branches, and utility values of events at terminal ends (leaves) of the branches.

The "tree structure of the decision tree" is a structure which is used in a clinical situation that involves decision making and in which individual actions such as treatments or tests to be selected are illustrated as branches and one or more events that occur as a result of these actions are further illustrated as branches.

The "branches" serve to represent, in the tree structure, actions selected by decision and events that occur as a result of the selected actions.

The "events that may possibly occur as a result of the selected actions" refer to a plurality of events that may possibly occur as a result of an action selected at a selection point of a decision item.

The "occurrence probabilities with which the respective events occur" refer to probabilities with which the events represented by the branches occur at a branching point (node) of the events.

The node is often referred to as a "probability point", which is a branching point in the decision tree where the event results are separated by stochastic processes.

The occurrence probabilities are determined by evidence. In the decision making support system of the present invention, the evidence is allowed to be dynamically renewable, i.e. renewable with the passage of time.

For example, evidence based on a standard database may be stored in the present system. The evidence may be renewed dynamically, namely in accordance with the passage of time, by introducing or correcting the latest data through a network such as the internet. The evidence may be renewed, for example, to conform to its own medical institution data by using a data base in the medical institution.

Further, the occurrence probabilities of the branches may be corrected to incorporate attribute information such as sex, age, and basic diseases of each person to be inspected, for example, a patient to be subjected to a medical treatment or test, by utilizing data base information having parameters such as sex, age, and basic diseases of the person to be inspected. Also, the occurrence probabilities of the branches may be corrected in accordance with the results of calculation on the degree of abnormality from an intrinsic normal state of each person to be inspected, by using a time series data of the person to be inspected.

The "event at a terminal end of each branch" is an event that is positioned at the terminal end (leaf) of the decision tree and may possibly occur eventually as a result of one or more selected actions.

The "utility values" are numerals that quantitatively represent the subjective sense of value of the person to be inspected on the events that may eventually occur (for example, the degree at which the person to be inspected desires the events to occur).

Various factors such as degree of health recovery (certainty of results of a treatment or test), sequela, pain of the treatment or test, period of time for the treatment or test or for staying in a hospital, life expectancy, costs of the treatment or test, and change in quality of life are reflected on the subjective sense of value of the person to be inspected in accordance with the situation.

The numerical values of the utility values may be simply given by the person to be inspected, or alternatively the result of a clinician's medical inquiry on the person to be inspected, for example, may be advantageously converted into numerical values by means of a method such as a fuzzy language interface.

These utility values are also dynamically renewable, i.e. renewable in accordance with the passage of time. For example, since the sense of value of the person to be inspected may change in accordance with the progress of the treatment or test and the circumstances thereof, the utility values must be renewable in accordance therewith. Therefore, it is preferable that the contents of the medical inquiry and the method of weighting for conversion of the utility values into numerical values are also renewable.

The "selection point" is a branching point at which a selection must be made in accordance with a judgment. An "expectation (expected value) of each branch" is a value calculated as a product of the occurrence probability of the branch and the utility value at the terminal end of the branch. This expectation, which reflects the subjective sense of value of the person to be inspected on the treatment or test as well as the objective evidence, is supplied as the judgment information.

Here, it is advantageous in making decisions if these expectations are displayed on the decision tree together with the utility values and the occurrence probabilities to improve overall visibility. However, if the expectations are to be re-calculated for use by repeatedly inputting the utility values and the like, it may be advantageous to display only the expectations and the utility values, or to display only some part of the decision tree together with the expectations and the utility values.

According to another aspect of the present invention, there is provided a support apparatus for making decisions on medical treatment plans or test plans, comprising: a decision tree preparing section for preparing a decision tree including branches that represent actions to be selected in deciding the medical treatment plans or test plans for a person to be inspected and events that may possibly occur as a result of the selected actions; an occurrence probability renewing section for dynamically renewing occurrence probabilities with which the respective events occur, by correction of the occurrence probabilities at appropriate times; a utility value renewing section for dynamically renewing utility values which reflect intentions of the person to be inspected on the events, by correction of the utility values at appropriate times; an expectation calculating section for calculating expectations of the actions to be selected in accordance with the occurrence probabilities of the branches and the utility values of the events; and a display section for displaying the decision tree, the occurrence probabilities of the branches, the utility values of the events, and the expectations of the actions to be selected.

EXAMPLES

Hereafter, with reference to FIGS. 1 to 5, an embodiment of a support system for making decisions on medical treatment plans or test plans according to the present invention will be explained.

Figure 1:
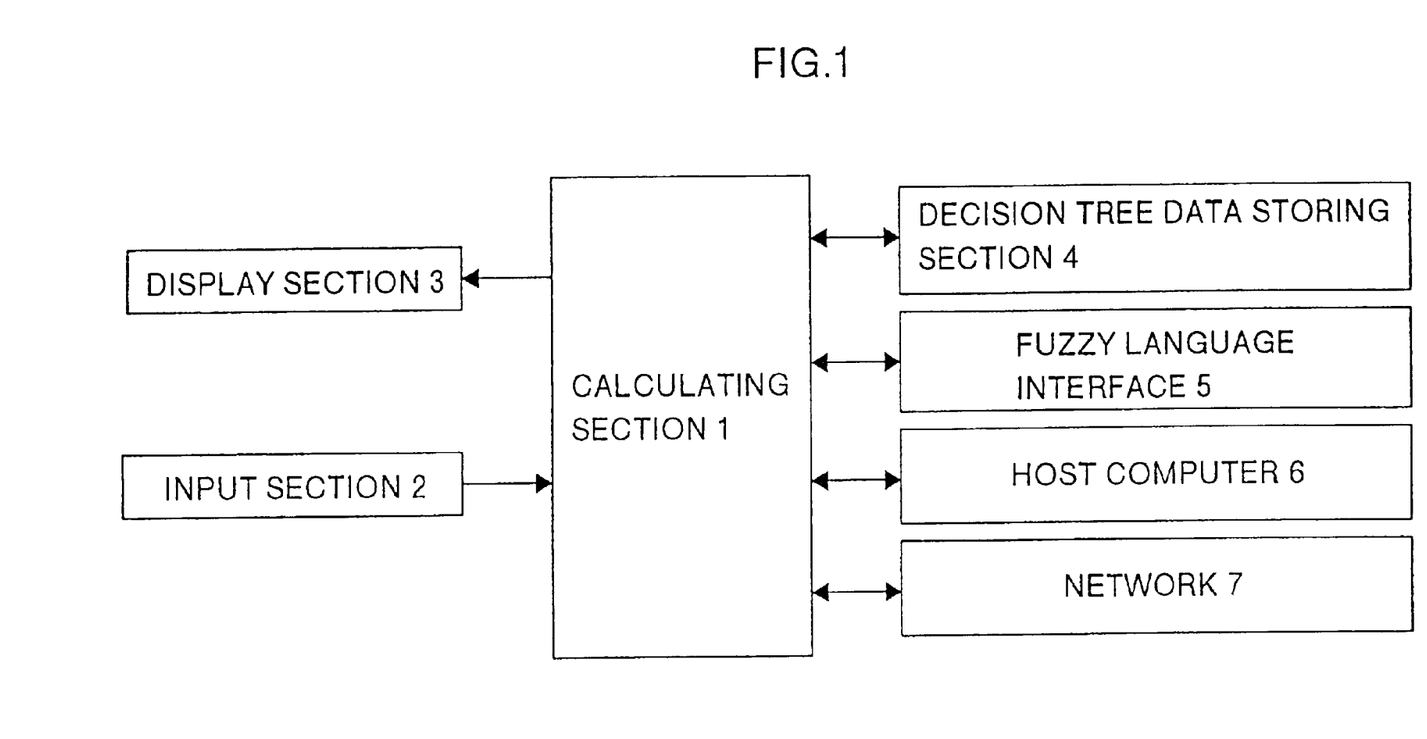
FIG. 1 is a block diagram of an apparatus as an embodiment of a support system for making decisions on medical treatment plans or test plans according to the present invention.
Figure 2:
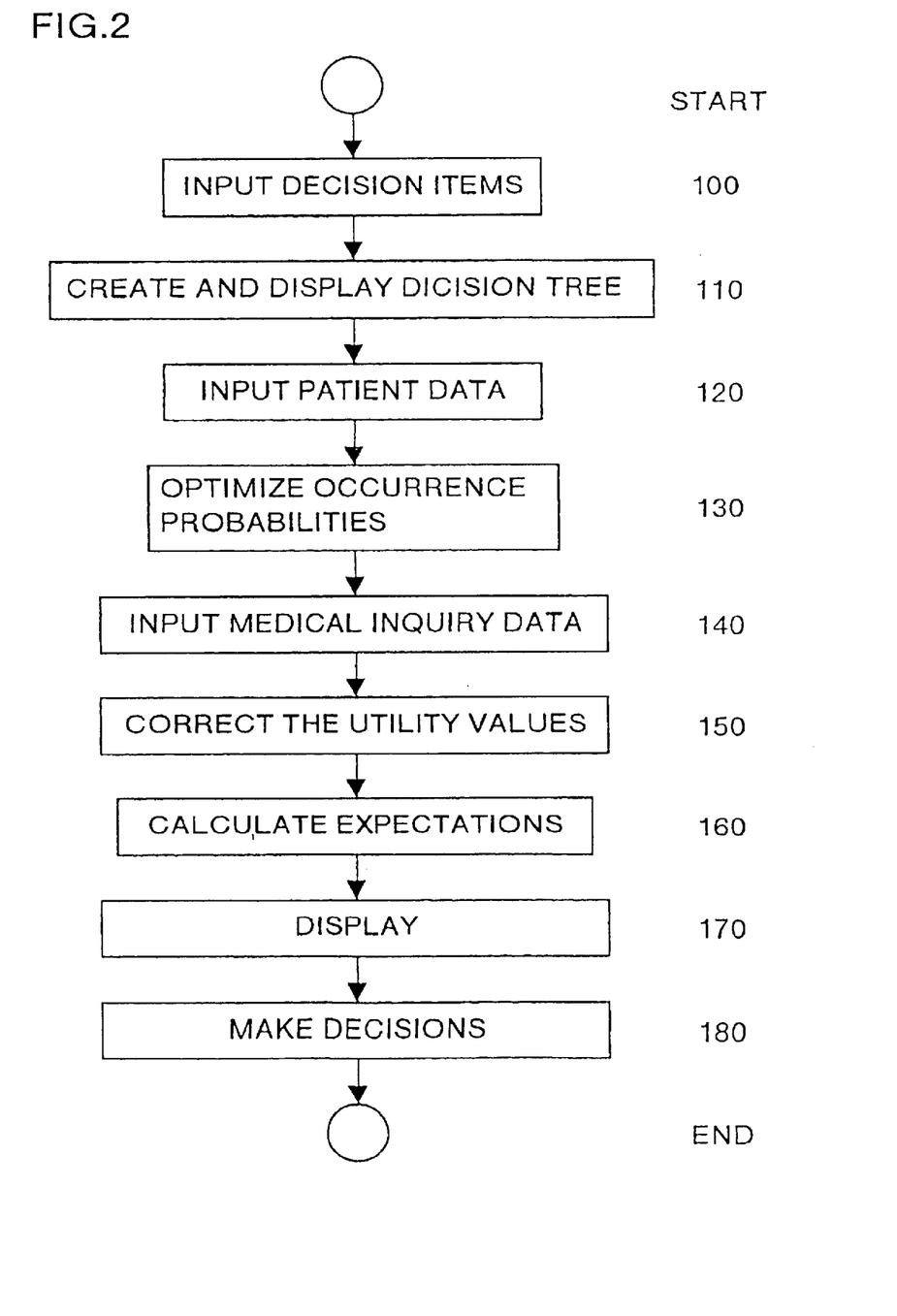
FIG. 2 is a flowchart showing a procedure for deciding a treatment on a person to be inspected by utilizing a method according to the support system of the present invention.

FIG. 1 is a block diagram of an apparatus as an embodiment of a support system for making decisions on medical treatment plans or test plans according to the present invention. FIG. 2 shows a procedure in deciding a treatment on a person to be inspected by using a method according to the support system of the present invention.

In a medical institution using the apparatus according to the present system, a decision tree data storing section 4 of the apparatus stores beforehand a standard decision tree, i.e. a tree structure including branches that represent actions such as treatments or tests to be selected and events that may possibly occur as a result of the actions together with the standard occurrence probabilities of the branches.

The occurrence probabilities may be obtained from a database which collectively contains various actions on treatment plans or test plans and the results of the actions as evidence. This database is constructed in such a manner that the occurrence probabilities may be renewed to the latest data dynamically, namely, in accordance with the passage of time, by downloading, for example, the latest data from a host computer 6, which is an external information source of the system, or from a network 7 at appropriate times.

Also, an inspection database of the medical institution may be received from the host computer 6 to be corrected into data adapted for the institution.

First, in order to decide the treatment plans or test plans to be carried out on the patient, decision items are input into the apparatus from an input section 2 (step 100). The decision items are, for example, a selection of a treatment of lumbago and the like. Then, the apparatus recalls a decision tree for making selections on the treatment of lumbago, which has been input as a decision item, from the decision tree data storage section 4.

Then, the apparatus displays on a display section 3 the decision tree including branches that represent the actions to be selected (surgical operation and conservation treatment) for deciding a treatment on lumbago and the events that may possibly occur (recovery, partially effective, death, and the like) as a result of the selected actions (step 110). The decision tree also shows the latest data of occurrence probabilities adapted for the institution.

Next, attribute information such as sex, age, weight, basic diseases, medical history, or test results of the patient, i.e. the person to be inspected, is input into the apparatus from the host computer 6 (step 120). Then, a calculating section (central processing unit) 1 of the apparatus renews (optimizes) the occurrence probabilities of the branches in the decision tree again in accordance with the attribute information of the patient and displays them on the display section 3 (step 130).

If the amount of data in the database is large, the data can be optimized to conform to the attribute information of the patient simply by extracting the group of data that belongs to the attribute information of the patient (for example, the age, group, sex, test results, and the like of the patient). However, by such extraction, the amount of data to be used will be small and the data without attribute information will not be used. Accordingly, if the amount of data is small, the reliability of the database may possibly decrease.

Therefore, the system may be allowed to incorporate the function of calculating the correlation between the attribute information and the occurrence probabilities to perform a more effective optimization of the data. For example, the correlation between each attribute information and the occurrence probabilities is calculated and displayed as shown in FIG. 5.

Figure 5:
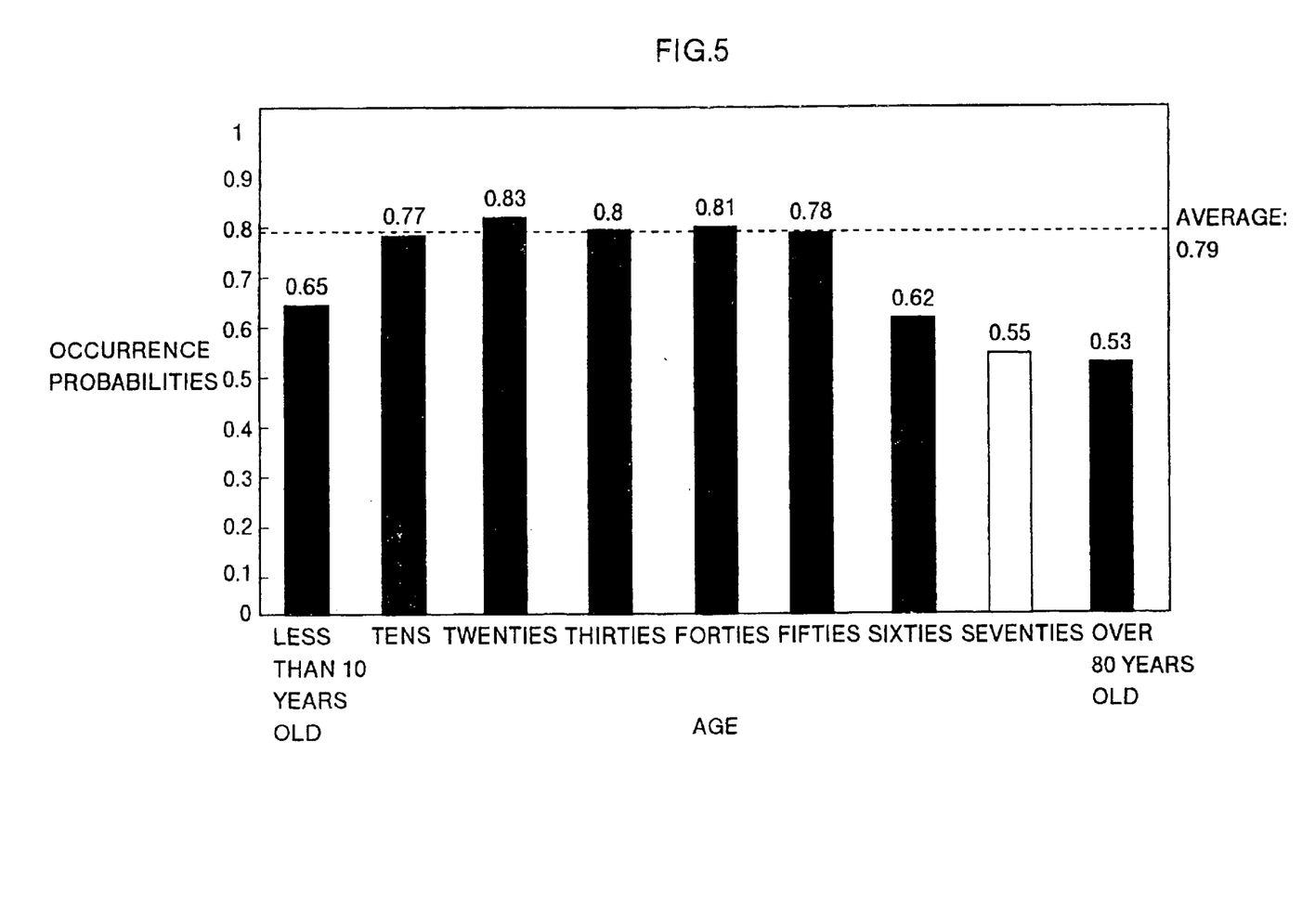
FIG. 5 is a view showing an example of correlation between the ages of patients and the occurrence probabilities.

FIG. 5 shows a correlation between the age and the occurrence probability, where the graph of the age group (seventies) to which the patient belongs is displayed in reverse, and the average occurrence probability for all ages (including the data in which the age information has not been input) is shown by a dotted line in FIG. 5.

The occurrence probability of the age group of the patient is 0.55, which is smaller by about 30% than the average occurrence probability of 0.79 for all ages. If the patient's age is within the range of tens to fifties, the correction of the data need not be particularly made. However, for this age group (seventies), the occurrence probability is considerably lower, so that the judgment of making decisions on the treatment plans may be different.

Thus, the correction of the attribute information and the occurrence probabilities is automatically made. If the correlation is displayed for each information, the clinician may decide whether the correction should be made or not by confirming the correlation and may use it in receiving the "informed consent" from the patient.

Also, since the treatment conditions within the same medical institution are similar, the occurrence probabilities may be calculated by weighting the data in the institution among the various data in the database, whereby the data may be optimized to conform to the attribute information of the patient.

Then, the clinician makes a medical inquiry to the patient on the actions such as the treatments or tests to be selected in making decisions and the events that may possibly occur as a result of the actions.

For example, the medical inquiry is made to confirm intentions of the patient as to whether the patient wishes a complete recovery by receiving a thorough treatment on lumbago, whether the patient wishes a moderate treatment that would reduce the pain which the patient suffers from at the moment, or whether the patient can endure a long term of staying in a hospital after receiving the surgical operation.

The medical inquiry is made for confirming the patient's intentions on the various conditions that may possibly occur as a result of the treatment rather than simply asking the patient directly as to which of the surgical operation and the conservation treatment is to be selected.

Then, the results of the medical inquiry are input into the apparatus from the input section 2 (step 140). The intentions of the patient are then converted into numerical values by a fuzzy language interface 5 in the apparatus in accordance with the results of the medical inquiry (step 150).

Once the utility values are determined, the calculating section 1 of the apparatus calculates the expectations based on the occurrence probabilities of the branches and the utility values of the events (step 160). The total decision tree including the utility values and the expectations thus obtained is displayed on the display section 3 (step 170). By viewing the decision tree on the display section 3, the clinician receives an informed consent from the patient and decides on whether a surgical operation or a conservation treatment is to be carried out (step 180).

Figure 3:
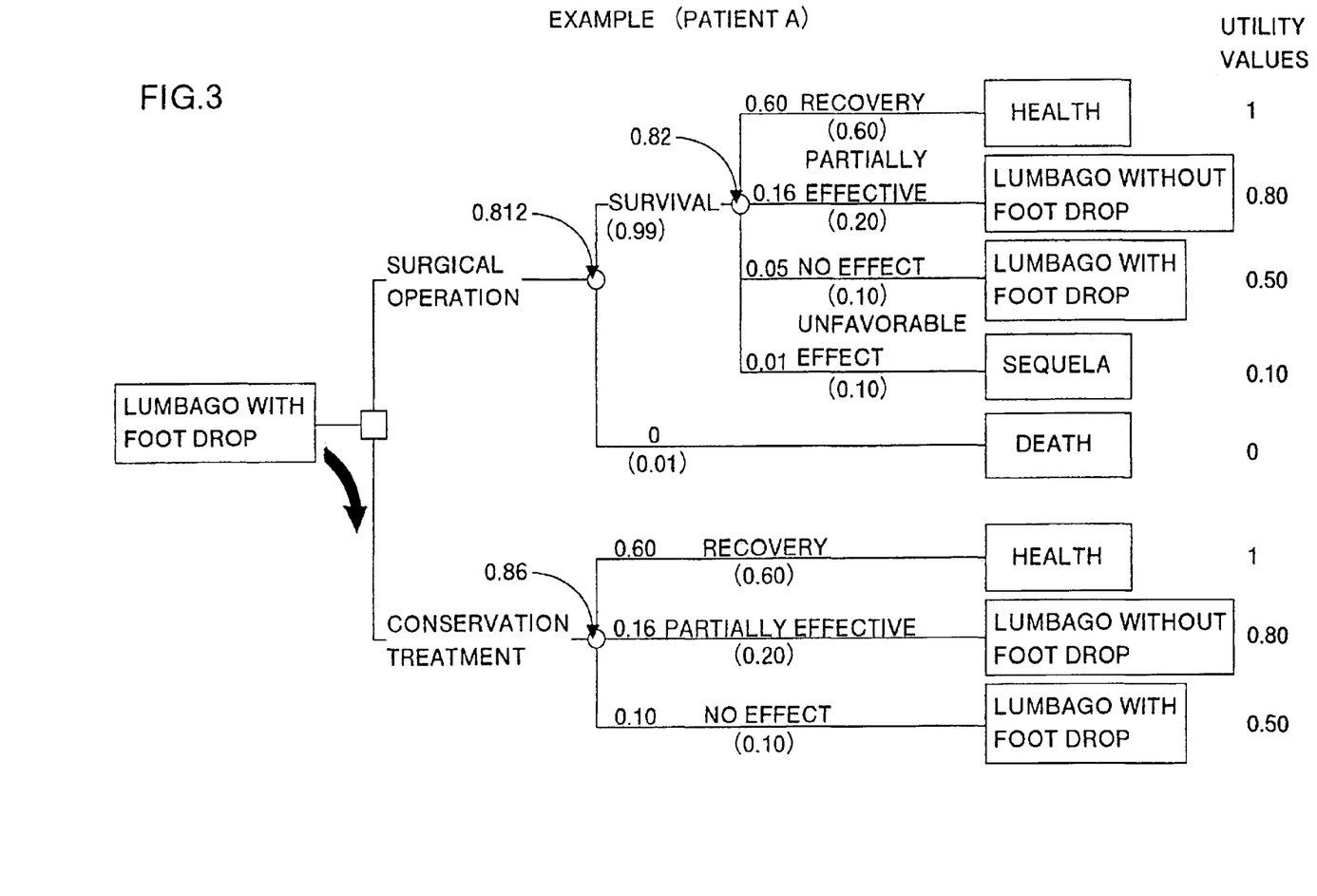
FIG. 3 is an example of a decision tree for a patient A as obtained by using the apparatus according to the support system of the present invention.

FIG. 3 shows a decision tree for a patient A with respect to treatments of lumbago according to the decision making support apparatus of the present invention. The selection points are represented by the symbol □. In this case, the decision item is the selection of whether the surgical operation or the conservation treatment is to be carried out. The nodes, which are represented by the symbol ○, are branching points of events that may possibly occur as a result of a selected action. In this case, "health", "lumbago without foot drop", "lumbago with foot drop", "sequela", and "death" shown at the terminal ends (leaves) of the branches are the events that may possibly occur.

The numerical values in the parentheses under the leaves branched from each node, i.e. 0.60, 0.20, 0.10, and 0.10, represent the occurrence probabilities of the branches. The numerical values on the right ends of the branches, i.e. 1, 0.80, 0.50, 0.10, and 0, represent the utility values of the events that may possibly occur for the patient. The numerical values drawn to nodes by arrow lines, i.e. 0.82, 0.812, and 0.86, represent expectations of the branches leading to the node.

The occurrence probabilities of the events that may possibly occur as a result of selected actions are renewed and corrected in accordance with the latest data and the institution data, to be displayed on the decision tree as the optimal evidence for the patient A on the basis of the attribute information of the patient A. In accordance with the result of a medical inquiry to the patient A, the utility values of the events are input for calculation of the expectations.

With respect to the patient A, the expectation for the case of the surgical operation is 0.812, which is lower than the expectation of 0.86 for the case of the conservation treatment. Therefore, it is found that the selection of the conservation treatment reflects the intentions of the patient more highly.

Figure 4:
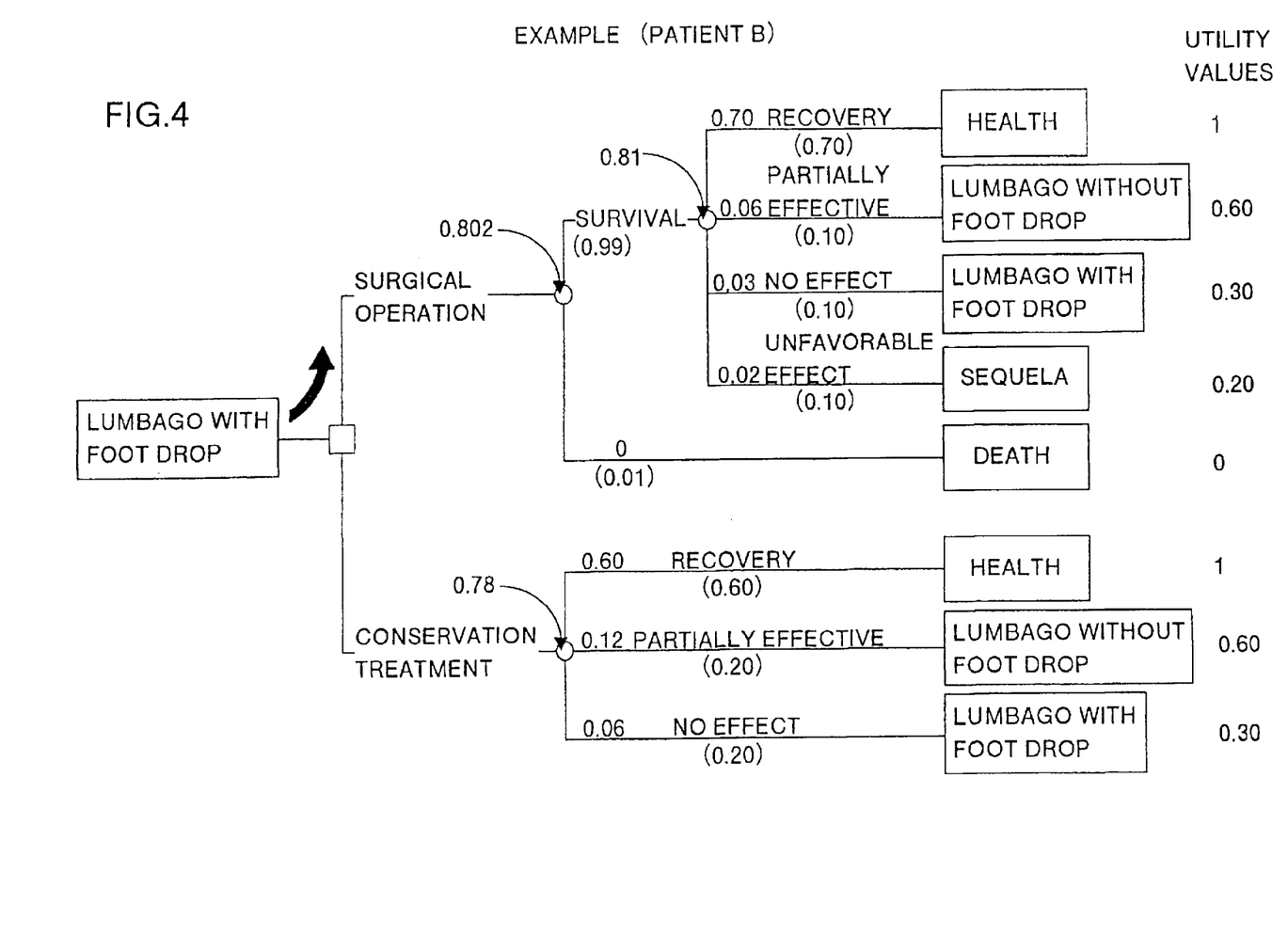
FIG. 4 is an example of a decision tree for a patient B as obtained by using the apparatus according to the support system of the present invention.

FIG. 4 shows a decision tree for another patient B with respect to the same decision item according to the decision making support apparatus of the present invention. In the case of the patient B, the occurrence probabilities corrected by the patient attribute information show that the recovery rate by conducting the surgical operation is higher as compared with the patient A. Further, since it is found out by the medical inquiry that the patient B strongly wishes a complete recovery by the treatment, the utility value (0.60 in this example) of the case of remaining lumbago without complete recovery and the utility value (0.30 in this example) of the case of remaining lumbago with foot drop are lower as compared with those of the patient B.

Thus, with respect to the patient B, the expectation of the surgical operation is 0.802, which is higher than the expectation of 0.78 for the case in which the conservation treatment is selected. Accordingly, it is found out that the selection of the surgical operation reflects the intentions of the patient more highly.

Thus, different judgment information is obtained for the same decision item depending on the patients. This is because the utility values, which represent the subjective sense of value of the patient, as well as the objective evidence, are reflected on the judgment by renewing the utility values and the objective evidence dynamically, namely in accordance with the passage of time.

The above judgment example is a simple selection case. However, even in a complex clinical situation such as a case in which a plurality of selection points are given or a case in which similar selections are repeatedly made at a certain interval, the decision tree may be changed in a similar manner to conform to the situation by dynamically renewing the occurrence probabilities and the utility values to the optimal evidence for the patient at that moment.

Although the present invention has fully been described by way of example with reference to the accompanying drawings, it is to be understood that various changes and modifications will be apparent to those skilled in the art. Therefore, unless otherwise such changes and modifications depart from the scope of the invention, they should be construed as being included therein.

What we claim is:

1. A support system for use in making decisions on medical treatment plans or test plans, said support system using a decision tree including branches that represent actions to be selected in deciding on a medical treatment plan or test plan for a person to be inspected and events that may occur as a result of the selected actions; and calculating expectations of the actions to be selected in accordance with occurrence probabilities for the respective events and utility values which reflect intentions of the person to be inspected on the events, wherein the occurrence probabilities of the branches are renewable in accordance with attribute information of the person to be inspected.

2. A support system according to claim 1, wherein the attribute information of the person to be inspected includes at least one of age, sex, weight, basic diseases, medical history, and test results of the person to be inspected.

3. A support system according to claim 1, wherein the utility values are calculated in accordance with data that includes at least one of certainty of results of a treatment or test, a degree of health recovery, sequela, costs of the treatment or test, pain of the treatment or test, length of the treatment or test or stay in a hospital, life expectancy, and change in quality of life.

4. A support system according to claim 3, wherein the utility values are calculated as numerical values in a plurality of ranks in accordance with the data in accordance with which the utility values are calculated.

5. A support system according to claim 3, wherein the one or more data items are based on a result of a medical inquiry on the intentions of the person to be inspected.

6. A support system according to claim 1, said system further displaying a correlation between the attribute information of the person to be inspected and the occurrence probabilities.

7. A support system according to claim 1, wherein said system is connected to a host computer for storing the attribute information of the person to be inspected.

8. A support system according to claim 1, wherein the occurrence probabilities are renewable in accordance with information from a network.

9. A support system for use in making decisions on medical treatment or test plans, comprising:
   a decision tree data storing section storing a decision tree, said decision tree having branches that represent available actions to be selected in deciding on a medical treatment or test plan for a patient and events that may occur upon selecting an available action; and
   a calculating section calculating expectation values for each available action of said decision tree based on occurrence probabilities for events that may occur upon selecting the corresponding available action and utility values associated with the events that may occur, such utility values reflecting the subjective worth the patient attributes to the corresponding events that may occur, wherein the occurrence probabilities for events that may occur upon selecting an available action are based on patient attribute information.

10. A support system according to claim 9, wherein the patient attribute information upon which the occurrence probabilities are based includes at least one of age, gender, weight, medical history, and test results.

11. A support system according to claim 9, wherein the utility values associated with each event that may occur upon selecting an available action are based on information that includes at least one of cost, certainty of event, degree of recovery, amount of pain, change in quality of life, length of hospital stay, and life expectancy associated with the event.

12. A support system according to claim 11, wherein the utility values for events that may occur upon selecting an available action are calculated as ranked numerical values in accordance with the information upon which the utility values are based.

13. A support system according to claim 11, wherein the utility values are further based on a result of an inquiry that determines the subjective preferences of the patient.

14. A support system according to claim 9, further comprising:

a display displaying a correlation between the patient attribute information and the occurrence probabilities associated with the events that may occur upon selecting an available action.

15. A support system according to claim 9, wherein said system is operatively connected to a host computer that stores the patient attribute information.

16. A support system according to claim 9, wherein occurrence probabilities associated with the events that may occur as a result of an available action are updated via a network.

17. A support system according to claim 16, wherein the network is the internet.

18. A method for use in deciding on medical treatment or test plans, comprising:

accessing a decision tree data structure that stores a decision tree, said decision tree having branches that represent available actions to be selected in deciding on a medical treatment or test plan for a patient and events that may occur upon selecting an available action;

receiving patient attribute information; and calculating expectation values for each available action of said decision tree based on occurrence probabilities for events that may occur upon selecting the corresponding available action and utility values associated with the events that may occur, such utility values reflecting the subjective worth the patient attributes to the corresponding events that may occur, wherein the occurrence probabilities used to calculate the expectation values are based on the received patient attribute information.

19. A method according to claim 18, wherein the received patient attribute information upon which the occurrence probabilities are based includes at least one of age, gender, weight, medical history, and test results.

20. A method according to claim 18, wherein the utility values associated with each event that may occur upon selecting an available action are based on information that includes at least one of cost, certainty of event, degree of recovery, amount of pain, change in quality of life, length of hospital stay, and life expectancy associated with the event.

21. A method according to claim 20, wherein the utility values for events that may occur upon selecting an available action are calculated as ranked numerical values in accordance with the information upon which the utility values are based.

22. A method according to claim 20, wherein the utility values are further based on a result of an inquiry that determines the subjective preferences of the patient.

23. A method according to claim 18, further comprising:

displaying a correlation between the patient attribute information and the occurrence probabilities associated with the events that may occur upon selecting an available action.

24. A method according to claim 18, wherein the patient attribute information is received and stored by a host computer.

25. A method according to claim 18, wherein occurrence probabilities associated with the events that may occur as a result of an available action are updated via a network.

26. A method according to claim 25, wherein the network is the internet.

* * * * *